United States Patent [19]

Barreau et al.

[11] Patent Number: 5,225,207
[45] Date of Patent: Jul. 6, 1993

[54] COMPLEXES DERIVED FROM PLATINUM, THEIR PREPARATION AND THE PHARMACEUTICAL COMPOSITIONS WHICH CONTAIN THEM

[75] Inventors: Michel Barreau, Montgeron; Jean-Claude Chottard, Nogent-sur-Marne; Jean-Bernard Le Peco, Paris; Patrick Mailliet, Fontenay-sous-Bois, all of France

[73] Assignee: Laboratoire Roger Bellon, France

[21] Appl. No.: 775,410

[22] Filed: Oct. 15, 1991

Related U.S. Application Data

[63] Continuation-in-part of Ser. No. 493,704, Mar. 14, 1990, abandoned.

[30] Foreign Application Priority Data

Mar. 17, 1989 [FR] France ............... 89 03511

[51] Int. Cl.$^5$ .................. A61K 33/24; C07F 15/00
[52] U.S. Cl. .................. 424/649; 514/184; 514/185; 546/2; 548/402; 549/3; 549/206; 556/16; 556/19; 556/137
[58] Field of Search ............ 556/16, 19, 137; 546/2; 548/402; 549/3, 206; 424/649; 514/185, 184

[56] References Cited

U.S. PATENT DOCUMENTS 4,562,275 12/1985 Speer et al. .................. 556/7
4,739,087 4/1988 Speer et al. .................. 556/137

FOREIGN PATENT DOCUMENTS 155705 9/1985 European Pat. Off. .
290169 11/1988 European Pat. Off. .

OTHER PUBLICATIONS

Chemical Abstracts, v. 109, No. 15, 10 Oct. 1988, Abst. No. 190186e, Georgiadis, et al. "Products from furans v. Synthesis of oxygen-containing isosteres of sympathomimetic amines via 6-hydroxy-2Hpyran-3(6H)-ones and their cis-platinum(II) complexes".
"Products from Furans v. Synthesis of Oxygen-Containing Isosteres of Sympathomimetic Amines via 6-Hydroxy-2H-pyran-3(6H)-ones and their cis-- Platinum (II) Complexes", Georgiadis et al, J. Heterocyclic Chem. vol. 25, 995 (1988).

Primary Examiner—José G. Dees
Assistant Examiner—Porfirio Nazario
Attorney, Agent, or Firm—Morgan & Finnegan

[57] ABSTRACT

New complexes of general formula (I) in which $R_1$ and $R_2$ together form a saturated or unsaturated polycyclic carbocyclic radical containing 7 to 12 carbon atoms, or a saturated or partially saturated mono-, bi- or tricyclic heterocyclic radical containing 5 to 11 chain members and a hetero-atom chosen from oxygen, sulphur or nitrogen, which latter atom can optionally be substituted by an alkoxycarbonyl radical, and, $X_1$ and $X_2$ represent chlorine atoms or together form either a radical of structure:

$$-O-\underset{\underset{O}{\|}}{C}-(CR_6R_7)_n-\underset{\underset{O}{\|}}{C}-O- \qquad (II)$$

in which n is 0 to 2 and $R_6$ and $R_7$, which are identical or different, are hydrogen atoms or, when $n=1$, can be alkyl radicals or form, together with the carbon atom to which they are attached, a cyclobutyl radical, or a radical of structure:

$$-O-\underset{\underset{O}{\|}}{C}-(CR_6R_7)_n-\underset{\underset{O}{\|}}{\overset{\overset{OH}{|}}{P}}-O- \qquad (III)$$

in which n, $R_6$ and $R_7$ are defined as above, or their salts where such exist, and their hydrates, their preparation and the pharmaceutical compositions which contain them.

$$R_1 \underset{}{\overset{R_2}{\diagup}} \underset{NH_2}{\overset{NH_2}{\diagdown}} \underset{}{\overset{Pt}{\diagup\!\!\!\diagdown}} \underset{X_2}{\overset{X_1}{\diagdown}} \qquad (I)$$

9 Claims, No Drawings

COMPLEXES DERIVED FROM PLATINUM, THEIR PREPARATION AND THE PHARMACEUTICAL COMPOSITIONS WHICH CONTAIN THEM

This application is a continuation-in-part of U.S. Ser. No. 07 493,704 filed Mar. 14, 1990, abandoned, which is hereby incorporated by reference.

The present invention relates to new complexes derived from platinum, of general formula:

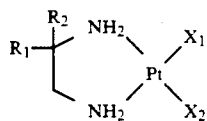

if appropriate their metal salts and their hydrates, their preparation and the pharmaceutical compositions which contain them.

In European Patent Application 290 169 platinum complexes of general formula:

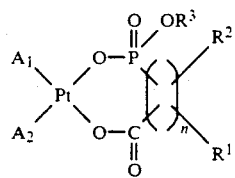

have been described in which:

$A_1$ and $A_2$ together form a radical of structure:

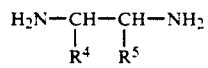

it being possible for $R^4$ and $R^5$ to be hydrogen atoms or optionally substituted alkyl radicals, $R^1$ and $R^2$ being in particular hydrogen or optionally substituted alkyl radicals, $R^3$ being in particular a hydrogen atom or a cation and n being 0 to 2.

These complexes are endowed with antitumour activity.

In Belgian Patent 900 842 diamino complexes of platinum have been described which have an antitumour activity and are of the general formula:

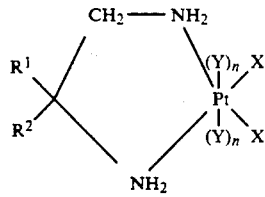

in which $R^1$ and $R^2$ together form an alkylene radical containing 3 to 6 carbon atoms and X in particular represents a halogen atom, or the 2 radicals X together form —OCO—COO— or —OCO—CHR$_3$—COO— radicals.

It has now been found that the complexes of general formula (I) in which:

$R_1$ and $R_2$ together form a saturated or unsaturated polycyclic carbocyclic radical containing 7 to 12 carbon atoms, or a saturated or partially saturated mono-, bi- or tricyclic heterocyclic radical which contains 5 to 11 chain members and a hetero-atom chosen from nitrogen, oxygen or sulphur and in which the nitrogen atom is optionally substituted by an alkoxycarbonyl radical, and, $X_1$ and $X_2$ represent chlorine atoms or together form either a radical of structure:

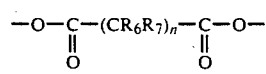

in which n is 0 to 2 and $R_6$ and $R_7$, which are identical or different, are hydrogen atoms or, when n=1, can be alkyl radicals or form, together with the carbon atom to which they are attached, a cyclobutyl radical, or a radical of structure:

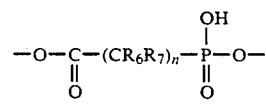

in which n, $R_6$ and $R_7$ are defined as above, and their salts where such exist, and their hydrates, show particularly valuable antitumour properties.

In the above definition, the alkyl and alkenyl radicals are straight-chain or branched and contain 1 to 4 carbon atoms and the halogen atoms can be chosen from chlorine, bromine, fluorine and iodine.

When $R_1$ and $R_2$ together form a polycyclic carbocyclic radical, by way of example, the latter can be chosen from: bicyclo[2.2.1]heptane, bicyclo[3.2.1.]octane, bicyclo[2.2.2]octane, bicyclo[3.2.2]nonane, bicyclo[3.3.1-]nonane, adamantane, decahydronaphthalene, tetrahydronaphthalene, spiro[5.5]undecane, tricyclo[5.2.1.0/2,6]decane or indane.

When $R_1$ and $R_2$ together form a saturated or partially saturated heterocyclic radical, by way of example, the latter can be chosen from: 4-chromanyl, 3-coumaryl, 4-homopiperidinyl, 4-piperidinyl, 3-pyrrolidinyl, 3-quinuclidinyl, 4-tetrahydropyranyl, 3-tetrahydrofuryl, 4-tetrahydrothiopyranyl, 3-tetrahydrothiofuryl or 4-tetrahydroquinolyl.

A/ According to the invention, the complexes of general formula (I) can be obtained by the action of potassium tetrachloroplatinate on a diamine of general formula:

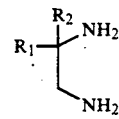

in which $R_1$ and $R_2$ are defined as above, followed where appropriate, when it is desired to obtain a complex of general formula (I) for which $X_1$ and $X_2$ are radicals of general formula (III) or (IV), by the conversion of the chlorinated complex obtained to a dicarboxylated or phosphonocarboxylated complex.

The action of potassium tetrachloroplatinate generally takes place under nitrogen and in the absence of light on the diamine, which is optionally liberated in situ from its salt, in an aqueous or aqueous-alcoholic (for example ethanol/water in proportions which can be up to 20-80 by volume) medium, at a temperature of between 0° and 80° C.

The conversion of the chlorinated complex to a dicarboxylated or phosphonocarboxylated complex takes place via the diaqua dinitrate complex of structure:

$$R_1 \underset{\phantom{x}}{\overset{R_2}{-}} \begin{matrix} NH_2 \\ \\ NH_2 \end{matrix} \underset{Pt^{2+}}{\diagup\diagdown} \begin{matrix} OH_2 \\ \\ OH_2 \end{matrix} \cdot 2NO_3^- \qquad (VI)$$

in which $R_1$ and $R_2$ are defined as above, which is then converted to the dicarboxylated or phosphonocarboxylated complex either by direct action of a salt of an acid of general formula:

$$\underset{O}{\overset{\phantom{x}}{HOC}} - (CR_6R_7)_n - \underset{O}{\overset{\phantom{x}}{COH}} \qquad (VIIa)$$

or $$\underset{O}{\overset{\phantom{x}}{HOC}} - (CR_6R_7)_n - \underset{O}{\overset{OH}{P}OH} \qquad (VIIb)$$

in which $R_6$, $R_7$ and n are defined as above, or by passage over an anion exchange resin (OH form) followed by the addition of an acid of general formula (VIIa) or (VIIb).

The complex of general formula (VI) can be obtained by the action of silver nitrate on the dichlorinated complex, in an aqueous medium or in an alcohol/water mixture (ethanol/water or methanol/water for example) in proportions which can vary, preferably, to up to 10% of methanol, the reaction being carried out under nitrogen and in the absence of light at a temperature of between 20° and 70° C.

The direct action of a salt of the acid of general formula (VIIa) or (VIIb) on the complex of general formula (VI) takes place in an aqueous or aqueous-alcoholic medium, in the absence of light and under an atmosphere of nitrogen, at a temperature of between 0° and 50° C.

It is not essential to isolate the complex of general formula (VI) to use it in this reaction.

The salt of the acid of general formula (VIIa) or (VIIb) is chosen, preferably, from the alkali metal salts (sodium or potassium salt for example); it can be formed in situ in the course of the reaction.

Under these conditions, the complex of general formula (I) for which $X_1$ and $X_2$ form a radical of general formula (IV) is obtained in the form of an alkali metal salt, which can be liberated and if desired converted into another salt by known methods.

When the complex of general formula (VI) is converted by passage over an anion exchange resin, the reaction is generally carried out by percolating the solution of diaqua dinitrate complex through a column of 1.2 to 1.5 times the theoretical amount of Amberlite IRA 402 resin (OH form) in the absence of light.

The addition of the acid of general formula (VIIa) or (VIIb) takes place in an aqueous medium, in the absence of light and under an atmosphere of nitrogen, at a temperature of between 0° and 50° C.

B/ According to the invention, the products of general formula (I) can also be obtained via the diiodo complex of general formula:

$$R_1 \underset{\phantom{x}}{\overset{R_2}{-}} \begin{matrix} NH_2 \\ \\ NH_2 \end{matrix} \underset{Pt}{\diagup\diagdown} \begin{matrix} I \\ \\ I \end{matrix} \qquad (VIII)$$

in which $R_1$ and $R_2$ are defined as above, by the action of potassium tetrachloroplatinate on a diamine of general formula (V), in the presence of an excess of potassium iodide. The diiodo complex obtained is then treated with silver nitrate and then with an alkali metal chloride in excess and subsequently, if appropriate, if it is desired to obtain a complex of general formula (I) for which $X_1$ and $X_2$ are radicals of general formula (III) or (IV), the chlorinated complex obtained is converted to a dicarboxylated or phosphonocarboxylated complex.

The preparation of the intermediate diiodo complex takes place under conditions identical to those described above for the preparation of a chlorinated platinum complex of general formula (I) by the action of potassium tetrachloroplatinate on an amine of general formula (V).

The addition of silver nitrate takes place under conditions analogous to those described above under A/.

The alkali metal chloride can be chosen from sodium or potassium chloride; it is not necessary to isolate the product formed as an intermediate in order to proceed to this addition. The reaction can be carried out at a temperature of between 0° and 70° C.

The conversion of the dichlorinated complex of general formula (I) to a dicarboxylated or phosphonocarboxylated complex is effected, if necessary, under the conditions described above under A/.

C/ According to the invention, the products of general formula (I) can also be obtained by the action of potassium trichloro(ethylene)platinate on a diamine of general formula (V), followed, if appropriate, when it is desired to obtain a product of general formula (I) in which $X_1$ and $X_2$ are radicals of general formula (III) or (IV), by the conversion of the chlorinated complex obtained to a dicarboxylated or phosphonocarboxylated complex.

The reaction generally takes place on the diamine (optionally liberated in situ from its salt), in an alcohol or in an aqueous-alcoholic medium, at a temperature of between 0° and 40° C.

The conversion of the dichlorinated complex obtained to a product of general formula (I) in which $X_1$ and $X_2$ are radicals of general formula (III) or (IV) takes place under the conditions described above under A/.

The diamines of general formula (V) can be prepared as described below in the examples, in particular by a Strecker reaction in the presence of sodium cyanide or potassium cyanide and ammonium chloride, ammonia or benzylamine, on a ketone of general formula:

$$\underset{R_1}{\overset{R_2}{\diagdown}} \!\!=\!\! O \qquad (IX)$$

in which $R_1$ and $R_2$ are defined as above, followed by catalytic hydrogenation of the aminonitrile formed and, where appropriate, the removal of the protective radical or radicals.

The Strecker reaction takes place in water or in an alcohol (methanol or ethanol for example) or in an aqueous-alcoholic medium, at a temperature of between 20° and 80° C.

The Strecker reaction can also be carried out in the presence of trimethylsilyl cyanide on a ketone of general formula (XVI), in an anhydrous medium and if appropriate in the presence of a catalytic amount of Lewis acid.

In this case, the reaction takes place with or without solvent, at a temperature of between −20° and +40° C. Where appropriate, the Lewis acid can be chosen from zinc iodide or cobalt chloride; the solvent can be chosen from diethyl ether or dipropyl ether, tetrahydrofuran, dichloromethane or chloroform.

The trimethylsilylated cyanohydrin thus obtained is treated with ammonia or benzylamine in solution in an alcohol (for example methanol or ethanol) at a temperature of between 20° C. and the reflux temperature of the reaction mixture. This method for carrying out the Strecker reaction is chosen more particularly in the case of highly obstructed ketones of general formula (XVI) (such as, for example, the ketones for which $R_1$ and $R_2$ together form a bicyclo[2.2.2]octane or bicyclo[3.2.2-]nonane cyclic radical or a quinuclidine).

In the reactions described above it is understood that, depending on the reactants employed, the aminonitrile obtained as an intermediate can be protected on the amine.

The hydrogenation can be effected equally on the aminonitrile in which the amine function is free or protected. It is also possible to protect the amine function before the catalytic hydrogenation. In this case, the protection is effected in particular by acylation (for example in accordance with Org. Synth., vol. IV, p. 5 and 6).

The catalytic hydrogenation of the aminonitrile generally takes place under a pressure of 100 to 4000 kPa in the presence of a catalyst, such as Adams platinum, Raney nickel or rhodium on alumina, at a temperature of between 20° and 80° C. and the reduction is carried out in an alcohol (ethanol or methanol for example), either in the presence of hydrochloric acid or in a basic medium (ammonia for example), or in acetic acid in the presence of acetic anhydride.

When the reduction is carried out in an acetic medium, it is necessary to remove the acetyl groups from the diamine obtained. This is carried out by acid treatment after the hydrogenation.

In the case of ketones of general formula (XVI) for which the ketone function is not in a plane of symmetry of the molecule, the Strecker reaction leads to a mixture of exocyclic and endocyclic racemates in which the exocyclic racemate is preponderant.

It is understood that the platinum derivatives of general formula (I) prepared from exocyclic or endocyclic diamines or their mixtures fall within the scope of the present invention.

The diamines of general formula (V) in the form of the pure exocyclic racemate can be obtained by successive recrystallizations of the intermediate aminonitrile.

The diamines of general formula (V) in the form of the pure endo racemate can be obtained from the corresponding endo amino acids of general formula:

in which $R_1$ and $R_2$ are defined as above and in which the amine function has been protected beforehand, by conversion of the acid function to an amide by known methods, followed by removal of the protective radical from the amine and reduction of the amide by the action of diborane under the conditions described in J. Org. Chem., 38(16), 2786 (1973) or J. Org. Chem., 42(16), 3153 (1982).

The amino acids of general formula (XVII) can be obtained from ketones of general formula (XVI) for which $R_1$ and $R_2$ are defined as above, by the action of ammonium carbonate and an alkali metal cyanide, in an aqueous-alcoholic medium at a temperature of between 50° and 100° C., followed by hydrolysis of the spirohydantoin thus obtained, by the action of an aqueous solution of barium hydroxide, in an autoclave at a temperature of between 120° and 200° C.

The new complexes according to the invention for which $X_1$ and $X_2$ together form a radical of general formula (IV) can be converted to metal salts. These salts can be obtained by the action of a metal base (for example an alkali metal or alkaline earth metal base) in an appropriate solvent.

Examples of pharmaceutically acceptable salts which may be mentioned are the salts with the alkali metals (sodium, potassium, lithium) or the salts with the alkaline earth metals (magnesium, calcium).

The new complexes according to the present invention can be purified, if desired, by physical methods such as crystallization or chromatography.

The products of general formula (I), and also their pharmaceutically acceptable salts and their hydrates, are particularly useful for the treatment of malignant tumours.

They have proved particularly active on graft tumours in mice: they are especially active at doses of between 4 and 120 mg/kg, administered intraperitoneally, against leukaemia L1210. Their maximum tolerated dose is between 10 mg/kg and doses higher than 120 mg/kg administered intraperitoneally to mice.

Products of particular value are those of general formula (I) for which $R_1$ and $R_2$ together form a polycyclic carbocyclic radical chosen from: bicyclo[2.2.1]heptane, adamantane, bicyclo[3.2.1]octane, bicyclo[2.2.-2]octane or tricyclo[5.2.1.0/2,6]decane and $X_1$ and $X_2$ represent chlorine atoms or a radical of structure (IV) in which $R_6$ and $R_7$ are hydrogen atoms or methyl radicals.

And amongst these products, the following products are of more particular value:

cis-(2-amino-2-aminomethyl-bicyclo[2.2.1]heptane)-dichloroplatinum, cis-(2-amino-2-aminomethyl-bicyclo[3.2.1]octane)-dichloroplatinum, cis-(2-amino-2-aminomethyl-adamantane)-dichloroplatinum, cis-(3-amino-3-aminomethyl-bicyclo[3.2.1]octane)-dichloroplatinum, and cis-(2-amino-2-aminomethyl-bicyclo[2.2.2]octane)-dichloroplatinum.

The following examples, given as non-limiting examples, illustrate the present invention:

EXAMPLE 1

Under an atmosphere of nitrogen and in the absence of light, 2-amino-2-aminomethyl-bicyclo[2.2.1]heptane dihydrochloride (1.49 g), in the form of the mixture of the exo and endo racemates in a ratio of (4/1), is dissolved in methanol (6 cc) and a 1N solution (14 cc) of sodium hydroxide in water. Potassium tetrachloroplatinate (2.84 g) in solution in water (14 cc) is added to the opalescent solution obtained, with stirring, in the course of 10 minutes.

Stirring is continued for 20 hours at 20° C. The precipitate formed is drained, washed with water (3×5 cc) and dried under reduced pressure (2.5 kPa) in the presence of phosphorus pentoxide. Cis-(2-amino-2-aminomethyl-bicyclo[2.2.1]heptane)-dichloroplatinum hydrate (2.48 g) is thus obtained, as a mixture of the exo and endo racemates in a ratio of (4/1), in the form of a yellow-beige powder which melts with decomposition at 331° C.

2-Amino-2-aminomethyl-bicyclo[2.2.1]heptane dihydrochloride, as a mixture of the exo and endo racemates in a ratio of (4/1), can be obtained in the following way:

2-Acetylamino-2-acetylaminomethyl-bicyclo[2.2.1]heptane (3 g), in the form of a mixture of the exo and endo racemates in a ratio of (4/1), in a 6N solution (100 cc) of hydrochloric acid in water is refluxed for 8 hours. The mixture is concentrated to dryness under reduced pressure (5.2 kPa), the residue from the evaporation is taken up in ethanol (50 cc) and diisopropyl ether (150 cc) is added dropwise. The precipitate obtained is drained on a glass frit, washed with a mixture of ethanol and diisopropyl ether (25/75 by volume) (20 cc) and then with diisopropyl ether (2×20 cc) and finally dried in an oven at 80° C. 2-Amino-2-aminomethyl-bicyclo[2.2.1]heptane dihydrochloride (2.53 g) is thus obtained in the form of white crystals which melt at 262°–4° C.

2-Acetylamino-2-acetylaminomethyl-bicyclo[2.2.1]heptane, as a mixture of the exo and endo racemates in a ratio of (4/1), can be obtained in the following way:

A solution of 2-acetylamino-2-cyano-bicyclo[2.2.1]heptane (6.05 g), in the form of the mixture of the exo and endo racemates in a ratio of (4/1), in acetic acid (100 cc) is charged into a 250 cc autoclave and acetic anhydride (6.4 cc) and Adams platinum oxide (0.6 g) are added. The mixture is subjected to catalytic hydrogenation at 50° C. for 5 hours, under an initial pressure of 4000 kPa. After cooling, the catalyst is filtered off on a bed of clarcel DIC and the filtrate is evaporated under reduced pressure (5.2 kPa).

The residue from the evaporation is recrystallized from a mixture of water and ethanol (90/10 by volume) (100 cc); 2-acetylamino-2-acetylaminomethyl-bicyclo[2.2.1]heptane (7.25 g) is thus obtained in the form of fine white crystals which melt at 192°–4° C.

2-Acetylamino-2-cyano-bicyclo[2.2.1]heptane, as a mixture of the exo and endo racemates in a ratio of (4/1), can be obtained in the following way:

2-Amino-2-cyano-bicyclo[2.2.1]heptane (7.98 g), in the form of the mixture of the exo and endo racemates in a ratio of (4/1), is dissolved in diethyl ether (100 cc) and acetic anhydride (5.7 cc) is added. After stirring for 20 hours at 20° C., the precipitate formed is drained and washed with diethyl ether (3×20 cc).

2-Acetylamino-2-cyano-bicyclo[2.2.1]heptane (9.25 g) is obtained in the form of fine white crystals which melt at 152°–3° C.

2-Amino-2-cyano-bicyclo[2.2.1]heptane can be obtained quantitatively, in the form of a colourless oil which crystallizes at about 0° C. and corresponds to a mixture of the exo and endo racemates in a ratio of (4/1), by neutralization of its hydrochloride. This hydrochloride can be obtained under the conditions described by H. S. TAGER et al., J. Amer. Chem. Soc., 94(3), 968–972 (1972).

EXAMPLE 2

Under an atmosphere of nitrogen and in the absence of light, cis-(2-amino-2-aminomethyl-bicyclo[2.2.1]heptane)-dichloroplatinum (0.81 g), in the form of the mixture of the exo and endo racemates in a ratio of (4/1), is suspended in methanol (2 cc) and water (18 cc), and silver nitrate (0.68 g) in water (6.8 cc) is then added. The mixture is stirred for 3 hours at 20° C., the silver chloride formed is filtered off on a glass frit and the filtrate is then clarified on a filter cartridge having a pore size of 3μ. The solution of (2-amino-2-aminomethyl-bicyclo[2.2.1]heptane)diaqua-platinum dinitrate is percolated through a column, having a diameter of 1.2 cm, containing Amberlite IRA 402 ion exchange resin in the OH form (0.0012 mole/cc) (6 cc). A solution of phosphonoacetic acid (0.28 g) in water (6 cc) is added to the solution of (2-amino-2-aminomethyl-bicyclo[2.2.1]octane)-aqua-hydroxoplatinum hydroxide thus obtained.

The mixture is chromatographed on a column 1 m in height and 2.5 cm in diameter containing Sephadex LH 20 (120 g), collecting fractions of 5 cc. The fractions between 415 and 455 cc are concentrated to dryness.

The sodium salt hexahydrate of cis-(2-amino-2-aminomethyl-bicyclo[2.2.1]heptane)phosphonoacetatoplatinum (0.89 g), as a mixture of the exo and endo racemates in a ratio of (4/1), is thus obtained in the form of bright white crystals which melt with decomposition at 314° C.

EXAMPLE 3

The procedure is as in Example 2, starting from cis-(2-amino-2-aminomethyl-bicyclo[2.2.1]heptane)dichloroplatinum (0.81 g), in the form of the mixture of the exo and endo racemates in a ratio of (4/1), in methanol (2 cc) and water (18 cc), and silver nitrate (0.68 g) in water (6.8 cc). After filtering off the silver chloride formed and clarifying the filtrate on a cartridge having a pore size of 3μ, a solution of 2,2-dimethylphosphonoacetic acid (0.35 g) in a 1N solution (6 cc) of sodium hydroxide in water is added to the solution of (2-amino-2-aminomethyl-bicyclo[2.2.1]heptane)diaquaplatinum dinitrate. The mixture is chromatographed on a column 2.5 cm in diameter containing Sephadex LH 20 (120 g), collecting fractions of 5 cc. The fractions between 410 and 465 cc are concentrated to dryness.

The sodium salt pentahydrate of cis-(2-amino-2-aminomethyl-bicyclo[2.2.1]heptane-(2,2-dimethylphosphonoacetato)platinum (0.89 g) is thus obtained as a mixture of the exo and endo racemates in a ratio of (4/1), in the form of bright white crystals which melt with decomposition at 311° C.

2,2-Dimethylphosphonoacetic acid can be prepared under the conditions described in Patent Application EP 290169.

EXAMPLE 4

The procedure is as in Example 1, starting from a solution of 2-amino-2-aminomethyl-adamantane dihydrochloride (3 g) in methanol (3 cc) and a 1N solution (24 cc) of sodium hydroxide in water, and a solution of potassium tetrachloroplatinate (4.98 g) in water (30 cc).

Cis-(2-amino-2-aminomethyl-adamantane)-dichloroplatinum (3.9 g) is thus obtained in the form of a yellow powder which melts with decomposition at 360° C.

2-Amino-2-aminomethyl-adamantane dihydrochloride can be obtained in the following way:

2-Acetylamino-2-acetylaminomethyl-adamantane (6.45 g) in a 6N solution (180 cc) of hydrochloric acid in water is refluxed for 6 hours. The solution is concentrated to dryness under reduced pressure (5.2 kPa), the residue from the evaporation is taken up in ethanol (100 cc) and diisopropyl ether (100 cc) is added dropwise.

The precipitate obtained is drained on a glass frit, washed with a mixture of ethanol and diisopropyl ether (50/50 by volume) (20 cc) and dried in an oven at 80° C. 2-Amino-2-aminomethyl-adamantane dihydrochloride (3.73 g) is thus obtained in the form of white crystals which melt at 300° C.

2-Acetylamino-2-acetylaminomethyl-adamantane can be prepared in the following way:

A solution of 2-acetylamino-2-cyano-adamantane (6.8 g) in acetic acid (90 cc) is charged into a 500 cc autoclave and acetic anhydride (5.8 cc) followed by Adams platinum oxide (0.68 g) are added. The mixture is subjected to catalytic hydrogenation, at 50° C. for 5 hours, under an initial pressure of 4000 kPa. After cooling, the catalyst is filtered off on a bed of clarcel DIC and the filtrate is evaporated under reduced pressure (5.2 kPa). The residue from the evaporation is recrystallized from water (100 cc).

2-Acetylamino-2-acetylaminomethyl-adamantane (6.95 g) is thus obtained in the form of fine white crystals which melt at 108° C.

2-Acetylamino-2-cyano-adamantane can be obtained in the following way:

2-Amino-2-cyano-adamantane (10 g) is dissolved in diethyl ether (100 cc) and acetic anhydride (5.8 cc) is added. After stirring for 20 hours at 20° C., the precipitate formed is drained and washed with diethyl ether (3×20 cc).

2-Acetylamino-2-cyano-adamantane (6.83 g) is thus obtained in the form of fine white crystals which melt at 140° C.

2-Amino-2-cyano-adamantane can be obtained in the following way:

Sodium cyanide (6.61 g) and ammonium chloride (14.44 g) are dissolved in water (150 cc) and ethanol (250 cc). A 28% solution (30 cc) of ammonia in water is added and 2-adamantanone (20 g) is then added in portions. The mixture is refluxed for 5 hours. After cooling to 0° C., the mixture is acidified to pH 1 by the addition of a 2N solution of hydrochloric acid in water. The adamantanone which has not reacted is drained on a glass frit and the filtrate is neutralized to pH 9 by the addition of a 2N solution of sodium hydroxide in water. The precipitate is drained on a glass frit, washed with water (5×20 cc) and dried under reduced pressure (2.5 kPa).

2-Amino-2-cyano-adamantane (16.1 g) is thus obtained in the form of white crystals which melt at 215° C.

EXAMPLE 5

The procedure is as in Example 1, starting from 2-amino-2-aminomethyl-bicyclo[3.2.1]octane dihydrochloride (1.31 g), in the form of the mixture of the exo and endo racemates in a ratio of (8/1), in methanol (3 cc) and a 1N solution (12 cc) of sodium hydroxide in water, and potassium tetrachloroplatinate -2.46 g) in solution in water (12 cc). Cis-(2-amino-2-aminomethyl-bicyclo[3.2.1]octane)dichloroplatinum hydrate (1.23 g) is thus obtained as a mixture of the exo and endo racemates in a ratio of (8/1), in the form of a yellow-beige powder which melts with decomposition at 326° C.

2-Amino-2-aminomethyl-bicyclo[3.2.1]octane dihydrochloride, as a mixture of the exo and endo racemates in a ratio of (8/1), can be obtained in the following way:

The procedure is as in Example 1, but starting from 2-acetylamino-2-acetylaminmethyl-bicyclo[3.2.1]octane (4.14 g), in the form of the mixture of the exo and endo racemates in a ratio of (8/1), in a 6N solution (100 cc) of hydrochloric acid in water for 18 hours under reflux; by taking up the residue from the evaporation in ethanol (30 cc) and diethyl ether (100 cc), 2-amino-2-aminomethyl-bicyclo[3.2.1]octane dihydrochloride (3.1 g) is obtained in the form of white crystals which melt at 284°-6° C.

2-Acetylamino-2-acetylaminomethyl-bicyclo[3.2.1]octane, as a mixture of the exo and endo racemates in a ratio of (8/1), can be obtained in the following way:

The procedure is as in Example 1, but starting from 2-acetylamino-2-cyano-bicyclo[3.2.1]octane (9 g), in the form of the mixture of the exo and endo racemates in a ratio of (8/1), in acetic acid (140 cc) and acetic anhydride (8.8 cc), in the presence of Adams platinum oxide (0.9 g); by chromatographing the residue from the evaporation on a column 5.5 cm in diameter containing silica gel (250 g), eluting with a mixture of ethyl acetate and ethanol (75/25 by volume) and collecting fractions of 100 cc. The fractions between 1400 and 3100 cc are concentrated to dryness. 2-Acetylamino-2-acetylaminomethyl-bicyclo[3.2.1]octane (9.75 g) is thus obtained in the form of fine white crystals which melt at 92°-3° C.

2-Acetylamino-2-cyano-bicyclo[3.2.1]octane, as a mixture of the exo and endo racemates in a ratio of (8/1), can be obtained in the following way:

The procedure is as in Example 1, but starting from 2-amino-2-cyano-bicyclo[3.2.1]octane (8.05 g), in the form of the mixture of the exo and endo racemates in a ratio of (8/1), in diethyl ether (150 cc) and acetic anhydride (5.6 cc); 2-acetylamino-2-cyano-bicyclo[3.2.1]octane (10.16 g) is obtained in the form of fine white crystals which melt at 78°-80° C.

2-Amino-2-cyano-bicyclo[3.2.1]octane, as a mixture of the exo and endo racemates in a ratio of (8/1), can be obtained quantitatively from its hydrochloride, which is itself prepared in the following way:

Bicyclo[3.2.1]octan-2-one (30 g) is dissolved in ethanol (300 cc) and a solution of potassium cyanide (18.2 g) and ammonium chloride (13.9 g) in water (300 cc) is added. After stirring for 6 days at 20° C., the ethanol is concentrated under reduced pressure (5.2 kPa) and the aqueous phase is extracted with diethyl ether (5×200 cc). The ethereal phase is washed with water (2×50 cc), dried over sodium sulphate and concentrated under reduced pressure (5.2 kPa) to a volume of 400 cc. Hydrogen chloride gas is then bubbled through the solution until it is saturated. The precipitate formed is drained, washed with diethyl ether (3×25 cc) and dried under reduced pressure (2.5 kPa). 2-Amino-2-cyano-bicyclo[3.2.1]octane hydrochloride (13.25 g) is thus obtained, as a mixture of the exo and endo racemates in a ratio of (8/1), in the form of fine white crystals which melt with decomposition at 202°-5° C.

EXAMPLE 6

The procedure is as in Example 1, starting from exo-3-amino-3-aminomethyl-bicyclo[3.2.1]octane dihydrochloride (1.14 g) in methanol (10 cc) and a 1N solution (10 cc) of sodium hydroxide in water, and potassium tetrachloroplatinate (2.08 g) in solution in water (21 cc).

Cis-(exo-3-amino-3-aminomethyl-bicyclo[3.2.1]octane)dichloroplatinum (1.32 g) is thus obtained in the form of a yellow powder which melts with decomposition at 332° C.

Exo-3-amino-3-aminomethyl-bicyclo[3.2.1]octane dihydrochloride can be obtained in the following way:

The procedure is as in Example 1, but starting from exo-3-acetylamino-3-acetylaminomethyl-bicyclo[3.2.1]octane (4 g) in a 6N solution (100 cc) of hydrochloric acid in water for 18 hours under reflux; by taking up the residue from the evaporation in ethanol (50 cc) and diethyl ether (100 cc), exo-3-amino-3-aminomethyl-bicyclo[3.2.1]octane dihydrochloride (2.15 g) is obtained in the form of white crystals which melt with decomposition at 296°-8° C.

Exo-3-acetylamino-3-acetylaminomethyl-bicyclo[3.2.1]octane can be obtained in the following way:

The procedure is as in Example 1, but starting from exo-3-acetylamino-3-cyano-bicyclo[3.2.1]octane (4 g) in acetic acid (60 cc) and acetic anhydride (3.8 cc) in the presence of Adams platinum oxide (0.5 g); concentrating to dryness, chromatographing on a column 5.5 cm in diameter containing silica gel (300 g), eluting with a mixture of ethyl acetate and ethanol (85/15 by volume) and collecting fractions of 100 cc. The fractions between 1200 and 1800 cc are concentrated to dryness; exo-3-acetylamino-3-acetylaminomethyl-bicyclo[3.2.1]octane (4.1 g) is thus obtained in the form of a colourless oil.

NMR spectrum (200 MHz, DMSO, δ in ppm); 8.00 (t, —CH$_2$—NH—CO—CH$_3$); 7.40 (s, —NH—CO—CH$_3$); 3.30 (d, —$\overline{\text{CH}}_2$—NH—CO—CH$_3$); 1.65 and 1.82 (2s, —CO—CH$_3$ and —CO—CH$_3$); 1.25 to 1.60 and 1.90 to 2.15 (complex, 12H of the cycle).

Exo-3-acetylamino-3-cyano-bicyclo[3.2.1]octane can be obtained in the following way:

The procedure is as in Example 1, but starting from exo-3-amino-3-cyano-bicyclo[3.2.1]octane (10 g) in diethyl ether (100 cc) and acetic anhydride (10 cc); concentrating to dryness, chromatographing the residue on a column 8 cm in diameter containing silica gel (500 g), eluting with a mixture of dichloromethane and ethyl acetate (90/10 by volume) and collecting fractions of 100 cc. The fractions between 1400 and 3000 cc are concentrated to dryness; exo-3-acetylamino-3-cyano-bicyclo[3.2.1]octane (8.69 g) is obtained in the form of a viscous colourless oil.

NMR spectrum (200 MHz, DMSO, δ in ppm); 8.35 (s, —NH—CO—CH$_3$); 1.90 (s, —CO—CH$_3$); 1.40 to 2.05 and 2.35 to 2.45 (complex, 12H of the cycle).

Exo-3-amino-3-cyano-bicyclo[3.2.1]octane can be obtained under the conditions described by H. CHRISTENSEN et al., J. Med. Chem., 26, 1374-8 (1983).

EXAMPLE 7

The procedure is as in Example 1, starting from 2-amino-2-aminomethyl-bicyclo[2.2.2]octane dihydrochloride (2.27 g) in methanol (15 cc) and a 1N solution (20 cc) of sodium hydroxide in water, and potassium tetrachloroplatinate (4.15 g) in solution in water (42 cc).

Cis-(2-amino-2-aminomethyl-bicyclo[2.2.2]octane)dichloroplatinum (1.93 g) is thus obtained in the form of a yellow-beige powder which melts with decomposition at 317° C.

2-Amino-2-aminomethyl-bicyclo[2.2.2]octane dihydrochloride can be obtained in the following way:

The procedure is as Example 1, but starting from 2-acetylamino 2-acetylaminomethyl-bicyclo[2.2.2]octane (4.6 g) in a 6N solution (100 cc) of hydrochloric acid in water for 48 hours under reflux; taking up the residue from the evaporation in ethanol (25 cc) and diethyl ether (75 cc), 2-amino-2-aminomethyl-bicyclo[2.2.2]octane dihydrochloride (3 g) is obtained in the form of white crystals which melt at 302°-303° C.

2-Acetylamino-2-acetylaminomethyl-bicyclo[2.2.2]octane can be obtained in the following way:

The procedure is as in Example 1, but starting from 2-acetylamino-2-cyano-bicyclo[2.2.2]octane (5.8 g) in acetic acid (100 cc) and acetic anhydride (5.6 cc) in the presence of Adams platinum oxide (0.6 g); chromatographing the residue from the evaporation on a column 5.5 cm in diameter containing silica gel (200 g), eluting with a mixture of ethyl acetate and ethanol (75/25 by volume) and collecting fractions of 50 cc. The fractions between 800 and 1750 cc are concentrated to dryness; 2-acetylamino-2-acetylaminomethyl-bicyclo[2.2.2]octane (5.45 g) is thus obtained in the form of a pale yellow viscous oil.

NMR spectrum (200 MHz, DMSO, δ in ppm); 7.35 (t, —CH$_2$—NH—CO—CH$_3$); 6.30 (s, —NH—CO—CH$_3$); 3.45 (d, —$\overline{\text{CH}}_2$—NH—CO—CH$_3$); 1.82 and 1.98 (2s, —CO—CH$_3$ and —CO—CH$_3$); 1.35 to 2.25 (complex, 12H of the cycle).

2-Acetylamino-2-cyano-bicyclo[2.2.2]octane can be obtained in the following way:

Bicyclo[2.2.2]octanone (9.92 g) is dissolved in diethyl ether (100 cc) and zinc iodide (0.5 g) is added and a solution of trimethylsilyl cyanide (10 g) in diethyl ether (20 cc) is then added to the suspension obtained. Stirring is continued for 30 minutes at between 20° and 25° C., a solution (120 cc), saturated at 0° C., of ammonia in methanol is then added and the suspension obtained is refluxed for 4 hours. The solvents are evaporated under reduced pressure (5.2 kPa), the residue is taken up in diethyl ether (150 cc), acetic anhydride (12 cc) is added and the mixture is stirred for 16 hours at 20° C. After concentrating the solvents, the residue is chromatographed on a column 10 cm in diameter containing silica gel (1500 g), eluting with a mixture of dichloromethane and ethyl acetate (90/10 for 5000 cc then 50/50 by volume) and collecting fractions of 50 cc. The fractions between 6050 and 6450 cc are concentrated to dryness; 2-acetylamino-2-cyano-bicycle[2.2.2]octane (5.9 g) is thus obtained in the form of a pale yellow viscous oil.

NMR spectrum (300 MHz, CDCl$_3$, δ in ppm); 5.9 (s, —NH—CO—CH$_3$); 2.05 (s, —CO—CH$_3$); 1.6 to 2.5 (complex, 12H of the cycle).

Bicyclo[2.2.2]octanone can be prepared under the conditions described by B. ROCHE et al., J. Org. Chem., 49(21), 3881-7 (1984).

EXAMPLE 8

The procedure is as in Example 1, starting from 8-amino-8-aminomethyl-tricyclo[5.2.1.0/2,6]decane dihydrochloride (0.37 g), in the form of the endo racemate, in methanol (5 cc) and a 1N solution (3 cc) of sodium hydroxide in water, and potassium tetrachloroplatinate (0.61 g) in solution in water (6 cc).

Cis-(8-amino-8-aminomethyl-tricyclo[5.2.1.0/2,6-]decane)dichloroplatinum (0.42 g) is thus obtained, as the endo racemate, in the form of a yellow-beige powder which melts with decomposition at 314° C.

8-Amino-8-aminomethyl-tricyclo[5.2.1.0/2,6]decane, in the form of the endo racemate, can be obtained in the following way:

8-Amino-tricyclo[5.2.1.0/2,6]decyl-8-carboxamide (0.40 g), in the form of the endo racemate, is suspended in anhydrous tetrahydrofuran (30 cc) and a 2N solution (5 cc) of "dimethyl borane-sulphide" complex in tetrahydrofuran is added dropwise. The solution obtained is refluxed for 20 hours; after cooling, a 2N solution (10 cc) of hydrochloric acid in diethyl ether is added. After concentrating to dryness, the powder obtained is dissolved in water (5 cc) and the pH is adjusted to 10 by the addition of sodium hydroxide as a 4N solution in water, in the presence of dichloromethane (10 cc). After decanting, the aqueous phase is reextracted with dichloromethane (2×5 cc) and the combined organic phases are washed with water (5 cc), dried over sodium sulphate and concentrated to dryness under reduced pressure (5.2 kPa).

The colourless oil obtained is dissolved in ethanol (5 cc) and a 2N solution (5 cc) of hydrochloric acid in diethyl ether is added. The precipitate formed is drained and washed with diethyl ether (2×2 cc). 8-Amino-8-aminomethyl-tricyclo[5.2.1.0/2,6]decane dihydrochloride (0.44 g) is obtained, as the endo racemate, in the form of white crystals which melt with decomposition at 282°–285° C.

8-Amino-tricyclo[5.2.1.0/2,6]decyl-8-carboxamide, in the form of the endo racemate, can be obtained in the following way:

The procedure is as in Example 11, but starting from a suspension of 8-benzyloxycarbonylamino-tricyclo[5.2.1.0/2,6]decyl-8-carboxamide (3.12 g), in the form of the endo racemate, in ethanol (300 cc) and a 1N solution (12 cc) of hydrochloric acid in water, in the presence of 10% palladium-on-charcoal (0.5 g) and under a hydrogen pressure of 140 kPa for 4 hours at 50° C. After filtering off the catalyst and concentrating the filtrate to dryness, taking up the residue in water (100 cc), rendering alkaline to pH 10 and extracting with dichloromethane, 8-amino-tricyclo[5.2.1.0/2,6]decyl-8-carboxamide (1.62 g) is thus obtained in the form of bright white platelets which melt at 131° C.

8-Benzyloxycarbonylamino-tricyclo[5.2.1.0/2,6]decyl-8-carboxamide, in the form of the endo racemate, is prepared in the following way:

The procedure is as in Example 11, but starting from 8-benzyloxycarbonylamino-tricyclo[5.2.1.0/2,6]decyl-8-carboxylic acid (4.8 g), in the form of the endo racemate, in anhydrous tetrahydrofuran (150 cc) and anhydrous triethylamine (2.05 cc); and isobutyl chloroformate (2.1 cc), followed by bubbling of ammonia. The precipitate formed is poured into water (200 cc), drained, washed with water (3×50 cc) and dried in an oven at 80° C. 8-Benzyloxycarbonylamino-tricyclo[5.2.1.0/2,6]decyl-8-carboxamide (3.11 g) is thus obtained in the form of a white powder which melts at 148° C.

8-Benzyloxycarbonylamino-tricyclo[5.2.1.0/2,6]decyl-8-carboxylic acid, in the form of the endo racemate, can be obtained in the following way:

The procedure is as in Example 11, but starting from 8-amino-tricyclo[5.2.1.0/2,6]decyl-8-carboxylic acid (5.3 g), in the form of a mixture of the endo and exo racemates in a ratio of (6/1), in a 1N solution (60 cc) of sodium hydroxide in water and benzyl chloroformate (3.85 cc). Extracting the excess benzyl chloroformate with diethyl ether, then acidifying the aqueous phase to pH 1 and extracting the oil, which then decants, with dichloromethane and recrystallizing the oily residue, after concentration, in a mixture of water and ethanol (30/70 by volume) (250 cc), 8-benzyloxycarbonylamino-tricyclo[5.2.1.0/2,6]decyl-8-carboxylic acid (4.98 g) is then obtained, as the endo racemate, in the form of a white powder which melts at 122° C.

8-Amino-tricyclo[5.2.1.0/2,6]decyl-8-carboxylic acid, in the form of a mixture of the endo and exo racemates in a ratio of (6/1), can be obtained under the conditions described by J. R. SUFRIN et al., Mol. Pharmacol., 15, 661–677 (1979).

EXAMPLE 9

The procedure is as in Example 1, starting from 8-amino-8-aminomethyl-tricyclo[5.2.1.0/2,6]decane dihydrochloride (0.80 g), in the form of the exo racemate, in methanol (5 cc) and a 1N solution (6 cc) of sodium hydroxide in water, and potassium tetrachloroplatinate (1.24 g) in solution in water (12 cc).

A cis-(8-amino-8-aminomethyl-tricyclo[5.2.1.0/2,6-]decane)dichloroplatinum (0.85 g) is thus obtained, as the exo racemate, in the form of a yellow-beige powder which melts with decomposition at 318° C.

8-Amino-8-aminomethyl-tricyclo[5.2.1.0/2,6]decane, in the form of the exo racemate, can be obtained in the following way:

The procedure is as in Example 1, but starting from 8-acetylamino-8-acetylaminomethyl-tricyclo[5.2.1.0/2,6]decane (1.97 g), in the form of the exo racemate, in a 6N solution (50 cc) of hydrochloric acid in water for 24 hours under reflux. Taking up the residue from the evaporation in ethanol (20 cc) and diethyl ether (80 cc), 6-amino-8-aminomethyl-tricyclo[5.2.1.0/2,6]decane dihydrochloride (1.26 g), is obtained, as the exo racemate, in the form of white crystals which melt at 273°–5° C.

8-Acetylamino-8-acetylaminomethyl-tricyclo[5.2.1.0/2,6]decane, in the form of the exo racemate, can be obtained in the following way:

The procedure is as in Example 1, but starting from 8-acetylamino-8-cyano-tricyclo[5.2.1.0/2,6]decane (5.8 g), in the form of the exo racemate, in acetic acid (100 cc) and acetic anhydride (5.6 cc), in the presence of Adams platinum oxide (0.6 g); recrystallizing the residue from the evaporation in a mixture of ethanol and water (25/75 by volume) (200 cc), 8-acetylamino-8-cyano-tricyclo[5.2.1.0/2,6]decane (4.33 g) is obtained, as the exo racemate, in the form of bright white crystals which melt at 204° C.

8-Acetylamino-8-cyano-tricyclo[5.2.1.0/2,6]decane, in the form of the exo racemate, can be obtained in the following way:

The procedure is as in Example 1, but starting from 8-amino-8-cyano-tricyclo[5.2.1.0/2,6]decane (4 g), in the form of the exo racemate, in diethyl ether (100 cc)

and acetic anhydride (3.85 cc); 8-acetylamino-8-cyano-tricyclo[5.2.1.0/2,6]decane (4.35 g) is obtained, as the exo racemate, in the form of fine white crystals which melt at 141° C.

8-Amino-8-cyano-tricyclo[5.2.1.0/2,6]decane, in the form of the exo racemate, is obtained quantatively from its hydrochloride, which can be obtained, in the form of the pure exo racemate, under the conditions described by J. R. SUFRIN et al., Mol. Pharmacol., 15, 661–677 (1979).

EXAMPLE 10

A solution of potassium tetrachloroplatinate (2.07 g) and potassium iodide (3.32 g) in water (20 cc) is brought to 80° C. for 15 minutes. The solution of potassium tetraiodoplatinate thus obtained is then added to a solution of 2-amino-2-aminomethyl-bicyclo[2.2.1]heptane dihydrochloride (1.06 g), in the form of the exo (1R, 2R, 4S) and (1S, 2S, 4R) racemate, in methanol (5 cc) and a 1N solution (10 cc) of sodium hydroxide in water. After stirring for 3 hours at 25° C. in the absence of light, the precipitate formed is drained on a glass frit, washed with water (3×5 cc) and then with acetone (5 cc); the diiodo complex (2.67 g) is thus obtained.

All of this complex is suspended in methanol (10 cc) and water (90 cc); silver nitrate (1.55 g) is added and the mixture is then stirred for 4 hours in the absence of light. After draining the silver iodide formed, the solution is clarified on a cartridge having a pore size of 3μ.

Potassium chloride (1.01 g) is added to the solution of diaqua platinum dinitrate thus obtained and the mixture is stirred for 4 hours in the absence of light. The precipitate formed is drained and washed with water (3×10 cc). Cis-(2-amino-2-aminomethyl-bicyclo[2.2.1]heptane)dichloroplatinum (1.34 g) is thus obtained, as the exo racemate monohydrate, in the form of a yellow-beige powder which melts with decomposition at 333° C.

2-Amino-2-aminomethyl-bicyclo[2.2.1]heptane dihydrochloride, in the form of the exo racemate, can be obtained in the following way:

The procedure is as in Example 3, but starting from 2-acetylamino-2-acetylaminomethyl-bicyclo[2.2.1]heptane (7.85 g), in the form of the exo racemate, in a 6N solution (250 cc) of hydrochloric acid in water for 8 hours under reflux; taking up the residue from the evaporation in ethanol (100 cc) and diethyl ether (300 cc), 2-amino-2-aminomethyl-bicyclo[2.2.1]heptane dihydrochloride (6.87 g) is obtained in the form of white crystals which melt at 271° C.

2-Acetylamino-2-acetylaminomethyl-bicyclo[2.2.1]heptane, in the form of the exo racemate, can be obtained in the following way:

The procedure is as in Example 3, but starting from 2-acetylamino-2-cyano-bicyclo[2.2.1]heptane (7.14 g), in the form of the exo racemate in acetic acid (250 cc) and acetic anhydride (7.5 cc), in the presence of Adams platinum oxide (0.7 g); taking up the residue from the evaporation in water and ethanol (80/20 by volume) (100 cc), 2-acetylamino-2-acetylaminomethyl-bicyclo[2.2.1]heptane (8.7 g) is thus obtained in the form of fine white crystals which melt at 208° C.

2-Acetylamino-2-cyano-bicyclo[2.2.1]heptane, in the form of the exo racemate, can be obtained in the following way:

The procedure is as in Example 3, but starting from 2-amino-2-cyano-bicyclo[2.2.1]heptane (6.33 g), in the form of the mixture of the exo and endo racemates in a ratio of (8/1), in diethyl ether (100 cc) and acetic anhydride (4.7 cc); after recrystallization from a mixture of ethanol and water (15/85 by volume) (300 cc), 2-acetylamino-2-cyano-bicyclo[2.2.1]heptane (7.14 g) is obtained in the form of fine white crystals which melt at 164° C.

Using the conditions described by H. S. TAGER et al., J. Amer. Chem. Soc., 94(3), 968–972 (1972), 2-amino-2-cyano-bicyclo[2.2.1]heptane melting at 232°–233° C. is obtained after two successive recrystallizations from the minimum of aqueous 1N solution of hydrochloric acid.

2-Amino-2-cyano-bicyclo[2.2.1]heptane can be obtained quantitively, in the form of a colourless oil which crystallizes at about 20° C. and corresponds to the mixture of the exo and endo racemates in a ratio of (8/1), by neutralization of its hydrochloride.

EXAMPLE 11

2-Amino-2-aminomethyl-bicyclo[2.2.1]heptane (0.098 g), in the form of the endo racemate, is dissolved, in the absence of light, in methanol (10 cc) and water (15 cc). A solution of potassium trichloro(ethylene)platinate (Zeise salt) (0.258 g) in methanol (5 cc) is added. The mixture is heated at 35° C. for 3 hours and stirring is then continued for 20 hours at 20° C. The precipitate formed is drained, washed with a mixture of methanol and water (50/50 by volume) (2×2.5 cc) and then with methanol (2.5 cc). Cis-(2-amino-2-aminomethyl-bicyclo[2.2.1]heptane)dichloroplatinum (0.150 g) is thus obtained, as the endo (1R, 2S, 4S) and (1S, 2R, 4R) racemate dihydrate, in the form of a yellow-beige powder which melts with decomposition at 322° C.

2-Amino-2-aminomethyl-bicyclo[2.2.1]heptane, in the form of the endo racemate, can be obtained in the following way:

2-Amino-bicyclo[2.2.1]heptyl-2-carboxamide (0.308 g), in the form of the endo racemate, is dissolved, under nitrogen, in anhydrous tetrahydrofuran (25 cc) and a 1N solution (10 cc) of diborane in anhydrous tetrahydrofuran is added. The mixture is refluxed for 20 hours; after cooling to 0° C., ethanol (20 cc) is added, followed, with care, by a 2N solution (5 cc) of hydrochloric acid in diethyl ether. The solvents are concentrated to dryness under reduced pressure (5.2 kPa), the residue is taken up in water (20 cc) and the mixture is rendered alkaline to pH 10 by the addition of a 1N solution of sodium hydroxide in water and then extracted with dichloromethane (3×20 cc). 2-Amino-2-aminomethyl-bicyclo[2.2.1]heptane (0.195 g) is thus obtained, in the form of a pale yellow oil; this diamine can be characterized by its hydrochloride, a white powder which melts at 291° C.

2-Amino-bicyclo[2.2.1]heptyl-2-carboxamide, in the form of the endo racemate, can be obtained in the following way:

2-Benzyloxycarbonylamino-bicyclo[2.2.1]heptyl-2-carboxamide (4.32 g), in the form of the endo racemate, is suspended in ethanol (150 cc) and a 1N solution (15 cc) of hydrochloric acid in water and 10% palladium-on-charcoal (0.5 g) is then added. The mixture is subjected to a hydrogen pressure of 140 kPa for 4 hours at 50° C. After cooling, filtering off the catalyst and concentrating the filtrate to dryness under reduced pressure (5.2 kPa), the residue is taken up in water (100 cc) and the mixture is rendered alkaline to pH 10 by the addition of a 2N solution of sodium hydroxide in water and extracted with dichloromethane (4×100 cc). 2-Aminobicyclo[2.2.1]heptyl-2-carboxamide (1.66 g) is thus obtained in the form of bright white platelets which melt at 178° C.

2-Benzyloxycarbonylamino-bicyclo[2.2.1]heptyl-2-carboxamide, in the form of the endo racemate, is prepared in the following way:

2-Benzyloxycarbonylamino-bicyclo[2.2.1]heptyl-2-carboxylic acid (11.6 g), in the form of the endo racemate, is dissolved in anhydrous tetrahydrofuran (200 cc) and anhydrous triethylamine (6.2 cc). After cooling to −20° C., isobutyl chloroformate (5.7 cc) is added and the white suspension obtained is stirred for 1 hour at between −20° and 0° C. and ammonia is then bubbled through, with stirring, at 0° C. until the mixture is saturated. Stirring is then continued for 16 hours at 20° C. and the precipitate formed is poured into water (700 cc), drained, washed with water (3×50 cc) and dried in an oven at 80° C. 2-Benzyloxycarbonylamino-bicyclo[2.2.1]heptyl-2-carboxamide (9.5 g) is thus obtained in the form of a white powder which melts at 188° C.

2-Benzyloxycarbonylamino-bicyclo[2.2.1]heptyl-2-carboxylic acid, in the form of the endo racemate is prepared in the following way:

2-Amino-bicyclo[2.2.1]heptyl-2-carboxylic acid (12.4 g), in the form of a mixture of the endo and exo racemates in a ratio of (12/1), is dissolved in a 1N solution (220 cc) of sodium hydroxide in water. After cooling to −10° C., benzyl chloroformate (18.3 cc) is added, the mixture is then stirred for 5 hours and the temperature is allowed to return from −10° to +20° C. The excess benzyl chloroformate is then extracted with diethyl ether (2×100 cc), the aqueous phase is then acidified to pH 1 by the addition of concentrated hydrochloric acid and the oil, which then decants, is extracted with dichloromethane (3×100 cc). After reconcentration of the dichloromethane under reduced pressure (5.2 kPa), the oily residue is recrystallized from a mixture of water and ethanol (65/35 by volume) (300 cc). 2-Benzyloxycarbonylamino-bicyclo[2.2.1]heptyl-2-carboxylic acid (13.5 g) is thus obtained in the form of a white powder which melts at 129° C.

2-Amino-bicyclo[2.2.1]heptyl-2-carboxylic acid, in the form of a mixture of the endo and exo racemates in a ratio of (12/1), can be obtained under the conditions described by H. N. CHRISTENSEN et al., J. Biol. Chem., 244(6), 1510–20 (1969).

EXAMPLE 12

One proceeds as in Example 1 starting with a solution of 1.506 g 2-amino-2-aminomethyl-7-oxabicyclo(2,2,1-)heptane dihydrochloride, in endoracemic form in 70 cm$^3$ of water, 14 cm$^3$ of a 1N solution of sodium hydroxide in water and a solution of 2.906 g potassium tetrachloroplatinate in 30 cm$^3$ of water.

One produces thus 1.915 g of the cis(2-amino-2-aminomethyl-7-oxabicyclo (2,2,1)heptane) dichloroplatinum in the endoracemic monohydrate form, in the form of a pale yellow powder which melts at 312° C. with decomposition.

One can obtain 2-amino-2-aminomethyl-7-oxabicyclo(2,2,1)heptane dihydrochloride, in the endoracemic form, as follows:

One dissolves, under nitrogen, a 1.405 g 2-amino-7-oxabicyclo(2,2,1)heptyl-2-carboxamide, in the endoracemic form, in 100 cm$^3$ of anhydrous tetrahydrofuran and one adds 27 cm$^3$ of a 2M solution of borane-dimethyl sulfide complex in tetrahydrofuran. One heats with reflux for 20 hours. After cooling, one adds 20 cm$^3$ of methanol and one concentrates to dryness under reduced pressure (5.2 kPa), and the residue is dissolved in 100 cm$^3$ of ethanol and treated with 0.5 g 50S black, then one adds 100 cm$^3$ of 0.5M solution of hydrochloric acid in diethyl ether. The crude dihydrochloride is centrifuged and then recrystallized in 150 cm$^3$ of ethanol. In this manner one produces 1.658 g of 2-amino-2-aminomethyl-7-oxabicyclo(2,2,1)-heptane dihydrochloride in the form of white crystals which melt at 282° C.

One can prepare 2-amino-7-oxabicyclo(2,2,1)heptyl-2-carboxamide, in the endoracemic form, as follows:

One operates as in Example 11, starting with 2.90 g 2-benzyloxycarbonylamino-7-oxabicyclo(2,2,1)heptyl-2-carboxamide, in the form of racemic endo compound, one obtains 1.54 g of 2-amino-7-oxabicyclo(2,2,1)heptyl-2-carboxamide, in the form of white crystals which melt at 129° C.

One can prepare 2-benzyloxycarbonylamino-7-oxabicyclo(2,2,1)heptyl-2-carboxamide, in the endoracemic form, as follows:

One operates as in Example 11, starting with 4.95 g 2-benzyloxycarbonylamino-7-oxabicyclo(2,2,1)heptyl-2-carboxylic acid, in the endoracemic form, in contrast to Example 11, the crude amide does not crystallize in the reaction medium after dilution with water. It is thus extracted four times with 75 cm$^3$ of ethyl acetate, then the combined organic phases are washed with 2 times 20 cm$^3$ of water, dried over sodium sulfate and concentrated to dryness at reduced pressure (5.2 Kpa). The residual oil is purified by chromatography on a column with a diameter of 4 cm containing 400 g of silica, using as eluant ethyl acetate and collecting fractions of 20 cm$^3$. The fractions between 780 and 2460 cm$^3$ are concentrated to dryness, one produces thus 3.52 g of 2-benzyloxycarbonylamino-7-oxabicyclo(2,2,1)heptyl-2-carboxamide in the form of a white powder which melts at 74.5° C.

One can prepare 2-benzyloxycarbonylamino-7-oxabicyclo(2,2,1)heptyl-2-carboxylic acid, in the endoracemic form, as follows:

One operates as in Example 11, starting with 4.09 g 2-amino-7-oxabicyclo(2,2,1)heptyl-2-carboxylic acid in the endoracemic form. In contrast to Example 11, the crude product extracted with dichloromethane is pure and does not require recrystallization. One produces thus 5.09 g of 2-benzyloxycarbonylamino-7-oxabicyclo(2,2,1)heptyl-2-carboxylic acid, in the form of a white powder with a melting point of 119° C.

One can prepare 2-amino-7-oxabicyclo(2,2,1)heptyl-2-carboxylic acid, in the endoracemic form, as follows:

One introduces, in 1000-cm$^3$ autoclave, 14.58 g of 5,5-spiro-2'-(7-oxabicyclo(2,2,1)heptyl)hydantoin, in the endoracemic form, 126.2 g octahydrate baryta and 400 cm$^3$ water, and one heats with stirring to 160° C. for 10 hours. After cooling, one pours the reaction medium over 600 cm$^3$ of water and one heats to reflux. Excess baryta is centrifuged at high temperature. One adds to the filtrate 6.6 g of ammonium carbonate, and then solid $CO_2$ until there is no longer any apparent precipitation. Then one again heats with reflux and one filters at high temperature the barium carbonate. One again adds 50 g of solid $CO_2$ to the filtrate and one heats to 50° C. for 1 hour. One again filters a small quantity of barium carbonate, and then one concentrates the filtrate to dryness under reduced pressure (2.5 kPa). One thus obtains, after drying in the over at 100° C., 12.15 g of 2-amino-7- oxabicyclo(2,2,1)heptyl-2-carboxylic acid, in the form of a white powder with a melting point of 298°-299° C.

One can obtain 5,5-spiro-2'-(7-oxabicyclo(2,2,1)heptyl-hydantoin, in the endoracemic form, as follows:

One dissolves, at approximately 30° C., 36.9 g ammonium carbonate in 450 cm³ of aqueous 50% ethanol, to which one adds, with stirring, 16.8 g of racemic 7-oxabicyclo(2,2,1)heptan-2-one, dissolved in 75 cm³ of 50% ethanol, and then one heats to 50° C. for 4 hours. One then adds 10.14 g potassium cyanide in 150 cm³ of 50% ethanol and one heats for 20 hours at 50° C. The reaction medium is concentrated at 150 cm³ and one cools to 5° C. for 2 hours. The crude precipitated spirohydantoin is then centrifuged, washed 3 times with 10 cm³ of water; it then contains approximately 5% of the exoracemic form. By recrystallization in 400 cm³ of water one obtains 19.65 g of 5,5-spiro-2'-7-oxabicyclo(2,2,1)heptylhydantoin, in pure endoracemic form, in the form of a white powder with a melting point of 306° C.

Racemic 7-oxabicyclo(2,2,1)heptan-2-one can be prepared according to P. Vogel, *Helv. Chim. Acta*, 1984, Vol. 67, pp. 1612-1615.

EXAMPLE 13

One proceeds as in Example 1, starting with a solution of 0.355 g of 2-amino-2-aminomethyl-7-oxabicyclo(2,2,1)heptane dihydrochloride in the form of dextrorotatory endoenantiomer, in 15 cm³ of water, 3.3 cm³ of a 1N aqueous solution of sodium hydroxide and a solution of 0.685 g of potassium tetrachloroplatinate in 5 cm³ of water.

In this manner one obtains 0.321 g of cis(2-amino-2-aminomethyl-7-oxabicyclo(2,2,1)heptane)dichloroplatinum, in the form of the dextrorotatory endoenantiomer monohydrate, in the form of a pale yellow powder which has a melting point of 303° C. with decomposition.

One can prepare 2-amino-2-aminomethyl-7-oxabicyclo(2,2,1)heptane dihydrochloride, in the form of the dextrorotatory endoenantiomer, as follows:

One proceeds as in Example 12, starting with 0.375 g 2-amino-7-oxabicyclo(2,2,1)heptyl-2-carboxamide, in the form of the dextrorotatory endoenantiomer. One thus obtains 0.421 g 2-amino-2-aminomethyl-7-oxabicyclo(2,2,1)heptane dihydrochloride, a dextrorotatory endoenantiomer, in the form of white crystals which melt at 280° C. and whose rotatory power in an aqueous solution at 0.5% is +8.5° (±0.4°), at 20° C. and 365 nm.

One can prepare 2-amino-7-oxabicyclo(2,2,1)heptyl-2-carboxamide, in the form of the dextrorotatory endoenantiomer, as follows:

One proceeds as in Example 11. Starting with 0.755 g of 2-benzyloxycarbonylamino-7-oxabicyclo(2,2,1)heptyl-2-carboxamide, in the form of the dextrorotatory endoenantiomer; one obtains 0.389 g of 2-amino-7-oxabicyclo(2,2,1)heptyl-2-carboxamide, in the form of the dextrorotatory endoenantiomer, in the form of white crystals with a melting point of 123° C.

One can obtain 2-benzyloxycarbonylamino-7-oxabicyclo(2,2,1)heptyl-2-carboxamide, in the form of the dextrorotatory endoenantiomer, by splitting the racemic form described in Example 12:

One subjects to chromatography in a column with diameter 5 cm and length 20 cm containing 250 g of cellulose type phase, 0.3 g of 2-benzyloxycarbonylamino-7-oxabicyclo(2,2,1)heptyl-2-carboxamide, in the endoracemic form, using as eluant a mixture of ethanol and hexane (25-75 by volume) at a flow rate of 30 cm³/min., with detection by UV absorption at 267 nm and collection of the fractions between 880 and 1035 cm³. By conducting 6 successive chromatographies as described above one obtains 0.810 g 2-benzyloxycarbonylamino-7-oxabicylclo(2,2,1)-heptyl-2-carboxamide, in the dextrorotatory endoenantiomer form, and in the form of white crystals with a melting point of 68° C. whose rotatory power in a 1% methanol solution is +30.3° C. (±0.6°), at 20° C. and 365 nm.

EXAMPLE 14

One proceeds as in Example 1, starting with a solution of 0.323 g of 2-amino-2-aminomethyl-7-oxabicyclo(2,2,1)heptane dihydrochloride, in the form of a dextrorotatory endoenantiomer, in 15 cm³ of water, 3 cm³ of a 1N aqueous solution of sodium hydroxide and a solution of 0.623 g of potassium tetrachloroplatinate in 5 cm³ of water.

One obtains thus 0.251 g of cis(2-amino-2-aminomethyl-7-oxabicyclo(2,2,1)heptane) dichloroplatinum, in the form of the levorotatory endoenantiomer monohydrate, in the form of a pale yellow powder which melts at 303° C. with decomposition.

One can obtain 2-amino-2-aminomethyl-7-oxabicyclo(2,2,1)heptane dihydrochloride, in the form of a levorotatory endoenantiomer, as follows:

One proceeds as in Example 12, starting with 0.406 g of 2-amino-7-oxabicyclo(2,2,1)heptyl-2-carboxamide, in the form of the levorotatory endoenantiomer. One thus obtains 0.347 g 2-amino-2-aminomethyl-7-oxabicyclo(2,2,1)heptane dihydrochloride, in the levorotatory endoenantiomer form, in the form of white crystals which melt at 280° C. and whose rotatory power in a 0.5% aqueous solution is −8.2° (±0.4°), at 20° C. and 365 nm.

One can prepare 2-amino-7-oxabicyclo(2,2,1)heptyl-2-carboxamide, in the levorotatory endoenantiomer form, as follows:

One proceeds as in Example 11. Starting with 0.798 g of 2-benzyloxycarbonylamino-7-oxabicyclo(2,2,1)heptyl-2-carboxamide, in the form of a levorotatory endoenantiomer, one obtains 0.420 g of 2-amino-7-oxabicyclo(2,2,1)heptyl-2-carboxamide, in the form of a levorotatory endoenantiomer, in the form of white crystals which melt at 123° C.

One can prepare 2-benzyloxycarbonylamino-7-oxabicyclo(2,2,1)heptyl-2-carboxamide, in the form of a levorotatory endoenantiomer, by splitting the racemic form described in Example 12:

One proceeds as in Example 13. By conducting 6 successive chromatographies on 0.3 g of the racemic form and with collection of the fractions between 750 and 850 cm³, one obtains 0.860 g 2-benzyloxycarbonylamino-7-oxabicyclo(2,2,1)heptyl-2-carboxamide, a levorotatory endoenantiomer, in the form of white crystals which melt at 68° C. and whose rotatory power in a 1% methanol solution is −30.2° (±0.6°), at 20° C. and 365 nm.

The present invention also relates to pharmaceutical compositions which contain, as active product, at least one product of general formula (I) in the pure state (in the free form or in the form of a salt) or in combination with one or more pharmaceutically acceptable adjuvants. These compositions can be used parenterally.

The compositions for parenteral administration can be sterile aqueous or non-aqueous solutions, or suspensions or emulsions. The solvent or vehicle used can be propylene glycol, a polyethylene glycol, vegetable oils, in particular olive oil, and injectable organic esters, for example ethyl oleate. These compositions can also contain adjuvants, in particular wetting agents, emulsifiers or dispersing agents. The sterilization can be effected in various ways, for example with the aid of a bacteriological filter, by incorporating sterilizing agents in the composition, by irradiation or by heating. They can also be prepared in the form of solid sterile compositions which will be dissolved at the time of use in sterile water or any other sterile injectable medium.

In human therapy, the medicaments according to the present invention are particularly useful for the treatment of cancers of the digestive system, lung cancers, cancers of the testicles or of the ovaries and also for the treatment of cancers of the head and the neck.

In a general manner, the physician will determine the dosage which he considers the most appropriate as a function of the age, the weight and all the other factors inherent to the subject to be treated.

The preferred mode of administration is intravenous. As an illustration, the medicaments according to the invention can be administered to man in an amount of 250 to 1000 mg/m² per treatment, intravenously.

The following example, given as a non-limiting example, illustrates a composition according to the present invention:

EXAMPLE

A 50 cc bottle containing cis-(1-amino-1-aminomethyl-bicyclo[3.2.1]octane)dichloroplatinum hydrate (835.3 mg) and an ampoule containing isotonic glucose serum (50 cc), intended to be added to the bottle at the time of use, are prepared.

The solution thus prepared, which contains 800 mg of cis-(1-amino-1-aminomethyl-bicyclo[3.2.1]octane)dichloroplatinum, is ready for incorporation in a perfusion liquid.

We claim:

1. A new complex derived from platinum, of general formula:

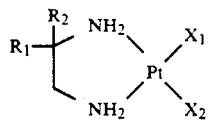

in which:

$R_1$ and $R_2$ together form a saturated or unsaturated polycyclic carbocyclic radical containing 7 to 12 carbon atoms, or a saturated or partially saturated mono-, bi- or tricyclic heterocyclic radical containing 5 to 11 chain members and a hetero-atom chosen from oxygen, sulphur or nitrogen, which latter atom can optionally be substituted by an alkoxycarbonyl radical, and, $X_1$ and $X_2$ represent chlorine atoms or together form either a radical of structure:

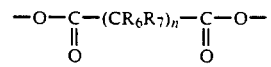

in which n is 0 to 2 and $R_6$ and $R_7$, which are identical or different, are hydrogen atoms or, when $n=1$, can be alkyl radicals or form, together with the carbon atom to which they are attached, a cyclobutyl radical, or a radical of structure:

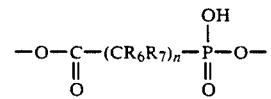

in which n, $R_6$ and $R_7$ are defined as above, it being understood that the abovementioned alkyl radicals and portions contain 1 to 4 carbon atoms in a straight or branched chain, and its hydrates and its salts where such exist.

2. A new complex derived from platinum according to claim 1, in which $R_1$ and $R_2$ together form a saturated polycyclic carbocyclic radical chosen from: bicyclo[2.2.1]heptane, bicyclo[3.2.1]octane, bicyclo[2.2.2]octane, bicyclo[3.2.2]nonane, bicyclo[3.3.1]nonane, adamantane, decahydronaphthalene, tetrahydronaphthalene, spiro[5.5]undecane, tricyclo[5.2.1.0/2,6]decane or indane, or $R_1$ and $R_2$ together form a heterocyclic radical chosen from: 4-chromanyl, 3-coumaryl, 4-homopiperidinyl, 4-piperidinyl, 3-pyrrolidinyl, 3-quinuclidinyl, 4-tetrahydropyranyl, 3-tetrahydrofuryl, 4-tetrahydrothiopyranyl, 3-tetrahydrothiofuryl or 4-tetrahydroquinolyl, and its hydrates and its salts.

3. A new complex derived from platinum according to claim 1, in which $R_1$ and $R_2$ together form a polycyclic carbocyclic radical chosen from: bicyclo[2.2.1]heptane, adamantane, bicyclo[3.2.1]octane, bicyclo[2.2.2]octane or tricyclo[5.2.1.0/2,6]decane and $X_1$ and $X_2$ represent chlorine atoms or a radical of structure:

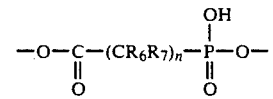

in which n is 1 and $R_6$ and $R_7$ are hydrogen atoms or methyl radicals or together form a cyclobutyl radical, and its hydrates and its salts.

4. Cis-(2-amino-2-aminomethyl-bicyclo[2.2.1]heptane)dichloroplatinum and its hydrated forms.

5. Cis-(2-amino-2-aminomethyl-bicyclo[3.2.1]octane)dichloroplatinum and its hydrated forms.

6. Cis-(2-amino-2-aminomethyl-adamantane)dichloroplatinum and its hydrates.

7. Cis-(3-amino-3-aminomethyl-bicyclo[3.2.1]octane)dichloroplatinum and its hydrates.

8. Cis-(2-amino-2-aminomethyl-bicyclo[2.2.2]octane)dichloroplatinum and its hydrates.

9. A pharmaceutical composition, which contains at least one complex derived from platinum according to claim 1, in the pure state, optionally in the form of a salt or hydrate or in combination with any compatible and pharmaceutically acceptable diluent or adjuvant.

* * * * *